(12) United States Patent
Fukuhara et al.

(10) Patent No.: US 12,036,308 B2
(45) Date of Patent: Jul. 16, 2024

(54) TRANSPARENT LIQUID COMPOSITION (71) Applicant: Shiseido Company, Ltd., Tokyo (JP)

(72) Inventors: Ryushi Fukuhara, Kanagawa (JP); Amelie Dauphin, Ormes (FR)

(73) Assignee: Shiseido Company, Ltd., Tokyo (JP)

( * ) Notice: Subject to any disclaimer, the term of this patent is extended or adjusted under 35 U.S.C. 154(b) by 550 days.

(21) Appl. No.: 17/291,161

(22) PCT Filed: Nov. 9, 2018

(86) PCT No.: PCT/JP2018/041614
§ 371 (c)(1),
(2) Date: May 4, 2021

(87) PCT Pub. No.: WO2020/095429
PCT Pub. Date: May 14, 2020

(65) Prior Publication Data
US 2022/0071888 A1   Mar. 10, 2022

(51) Int. Cl.
*A61K 8/92* (2006.01)
*A61K 8/86* (2006.01)
*A61Q 13/00* (2006.01)

(52) U.S. Cl.
CPC .............. *A61K 8/922* (2013.01); *A61K 8/86* (2013.01); *A61Q 13/00* (2013.01); *A61K 2800/30* (2013.01); *A61K 2800/49* (2013.01)

(58) Field of Classification Search
CPC .......... A61Q 13/00; A61K 8/922; A61K 8/86; A61K 2800/49; A61K 2800/30; A61K 2800/262; A61K 2800/5922
USPC .......................................................... 512/1
See application file for complete search history.

(56) References Cited

U.S. PATENT DOCUMENTS

| | | | |
|---|---|---|---|
| 2002/0132743 A1* | 9/2002 | Saito | C11D 3/2068 510/147 |
| 2005/0180942 A1 | 8/2005 | Shimizu et al. | |
| 2009/0202446 A1 | 8/2009 | Vlad et al. | |
| 2018/0258370 A1* | 9/2018 | Solinas | A61K 8/347 |

FOREIGN PATENT DOCUMENTS

| | | |
|---|---|---|
| CN | 101461771 A | 6/2009 |
| EP | 3 372 282 A1 | 9/2018 |
| JP | 08-176587 A | 7/1996 |
| JP | 1996176587 * | 7/1996 |
| JP | 2004-238376 A | 8/2004 |
| JP | 2004238376 * | 8/2004 |
| JP | 2005-288427 A | 10/2005 |
| JP | 2009-091271 A | 4/2009 |
| JP | 2010-132567 A | 6/2010 |
| JP | 2011-038030 A | 2/2011 |
| JP | 2011-120985 A | 6/2011 |
| JP | 2011-030793 A | 3/2018 |
| WO | WO-2007/125460 A1 | 11/2007 |

OTHER PUBLICATIONS

Keiko et al, JP 1996176587 Machine Translation, Jul. 9, 1996 (Year: 1996).*
Shimizu et al, JP 2004-238376 Machine Translation, Aug. 26, 2004 (Year: 2004).*
Marszall et al., "The Effect of Glycols on the Hydrophile-Lipophile Balance and the Micelle formation of Nonionic Surfactants," J.Am. Oil Chem. Soc., Feb. 1982, 59(2):84-87.

* cited by examiner

*Primary Examiner* — Jessica Whiteley
(74) *Attorney, Agent, or Firm* — Foley & Lardner LLP

(57) ABSTRACT

A transparent liquid composition that does not substantially contain ethyl alcohol, contains water as the main solvent, and has a high concentration of perfume is provided.

The transparent liquid composition comprises: (a) 3-20% by mass of a perfume component; (b) a hydrogenated castor oil to which 30-60 moles of polyoxyethylene is added; (c) an alkanol obtained by addition polymerization of 20-30 moles of polyoxyprolylene and 20-30 moles of polyoxyethylene; (d) one type or more of a surfactant having an Inorganic-value/Organic-value of 0.70-1.20; and (e) 40% by mass or greater of an aqueous component other than ethyl alcohol, wherein the blending ratio (d/(b+c)) of the component (d) to the sum of the blending amounts of the components (b) and (c) is 0.03-0.60, and ethyl alcohol is not substantially contained.

10 Claims, 2 Drawing Sheets

TRANSPARENT LIQUID COMPOSITION

CROSS-REFERENCE TO RELATED APPLICATIONS

This application is the U.S. National Stage of PCT/JP2018/041614, filed Nov. 9, 2018.

TECHNICAL FIELD

The present invention relates to a transparent liquid composition, and particularly to a fragrance that does not substantially contain ethyl alcohol.

BACKGROUND ART

Fragrance products are usually those that contain ethyl alcohol as the main solvent and are obtained by dissolving various perfumes. However, since there are people that are sensitive to ethyl alcohol, consumers who consider that safety is important tend to prefer products of which use of ethyl alcohol is refrained as much as possible. Furthermore, since ethyl alcohol was designated as the volatile organic compound (abbreviated as VOC) of which the amount of emission should be regulated by Amendment of Air Pollution Control Act in 2004, reduction of its usage is a social problem.

From such circumstances, products that does not substantially contain ethyl alcohol (hereinafter may be referred to as non-alcohol fragrance products) has been developed actively in the market of fragrances.

In non-alcohol fragrance products that have already been launched, there are those that contain an oil component as the main solvent (e.g., Patent Literature 1), and those that contain water as the main solvent.

Perfumes usually used in fragrance products are mixtures of oily components of different polarities; therefore, perfumes can be stably dissolved at a large amount when the main solvent is an oil component. However, oiliness is felt upon use in these products, and there are many consumers that do not prefer oiliness.

On the other hand, problems of oiliness do not basically occur in those that contain water as the main solvent; however, contrivance for stably blending perfumes, which are originally not compatible with water, in water is necessary. Perfumes are usually solubilized or emulsified with surfactants; however, since stickiness occurs as the blending amount of the surfactant increases, its usage is limited. Since it is difficult to solubilize a large amount of perfume, and also difficult to finely emulsify perfume depending on its type, the appearance becomes white-clouded and a problem of being avoided by consumers occurs. This is because beauty of the appearance is an important evaluation standard of fragrance products for consumers.

Accordingly, the main stream in transparent non-alcohol fragrance products containing water as the main solvent are those that have a low concentration of perfume (5% or less) in current market.

From such circumstances, a technique of producing a liquid composition that does not substantially contain ethyl alcohol, contains water as the main solvent, has a transparent appearance, and has a high concentration of perfume has been strongly demanded.

CITATION LIST

Patent Literature

Patent Literature 1: Japanese Unexamined Patent Publication No. 2010-132567A

SUMMARY OF INVENTION

Technical Problem

The present invention has been made in view of the problems of the above-mentioned conventional art, and a problem to be solved is to provide a transparent liquid composition that does not substantially contain ethyl alcohol, contains water as the main solvent, and has a high concentration of perfume.

Solution to Problem

As a result of diligent research to solve the above-mentioned problem, the Inventors have found that it is possible to stably dissolve a large amount of perfume in water by: having PEG-40 Hydrogenated Castor Oil and PPG-26-Buteth-26 as a main solubilizer and a surfactant having an IOB value of 0.70-1.20 as an auxiliary solubilizer; and using them together at a blending ratio of the auxiliary solubilizer to the main solubilizer (auxiliary solubilizer/main solubilizer) within a range of 0.03-0.60, thus accomplished the present invention.

That is, the present invention includes the following.

[1] A transparent liquid composition comprising:
   (a) 3-20% by mass of a perfume component;
   (b) a hydrogenated castor oil to which 30-60 moles of polyoxyethylene is added;
   (c) an alkanol obtained by addition polymerization of 20-30 moles of polyoxyprolylene and 20-30 moles of polyoxyethylene;
   (d) one type or more of a surfactant having an Inorganic-value/Organic-value of 0.70-1.20; and
   (e) 40% by mass or greater of an aqueous component other than ethyl alcohol,
   wherein the blending ratio (d/(b+c)) of the component (d) to the sum of the blending amounts of the components (b) and (c) is 0.03-0.60, and
   ethyl alcohol is not substantially contained.

[2] The transparent liquid composition of [1], wherein the surfactant of the component (d) has the square root of the sum of the square of the inorganic value and the square of the organic value of 2000-5000.

[3] The transparent liquid composition of [1] or [2], wherein the blending ratio (a/(b+c+d)) of the component (a) to the sum of the blending amounts of the components (b)-(d) is 0.4-1.1.

[4] The transparent liquid composition of any one of [1]-[3], wherein the component (d) is one type or more of a surfactant selected from a group consisting of: decyltetradecanol and phytosterol obtained by addition polymerization of ethylene oxide and propylene oxide; and polyoxyethylene hydrogenated castor oil esterified with pyroglutamic acid and isostearic acid.

[5] The transparent liquid composition of any one of [1]-[4], wherein the component (b) is PEG-40 Hydrogenated Castor Oil.

[6] The transparent liquid composition of any one of [1]-[5], wherein the component (c) is PPG-26-Buteth-26.

[7] The transparent liquid composition of any one of [1]-[6], wherein the blending ratio (c/b) of the component (c) to the blending amount of the component (b) is 0.7-2.5.

[8] The transparent liquid composition of any one of [1]-[7], wherein an oil component other than the perfume component (a) is not substantially contained.

Advantageous Effects of Invention

The present invention provides a transparent liquid composition that does not substantially contain ethyl alcohol, contains water as the main solvent, and has a high concentration of perfume.

DESCRIPTION OF EMBODIMENTS

Preferred embodiments of the present invention are described in the following.

"Non-alcohol" as used herein means that "ethyl alcohol is not substantially contained", and the term "substantially" as used herein means 5% by mass or less, preferably 3% by mass or less, more preferably 2% by mass or less, and most preferably 1% by mass or less. Since there are cases that commercially available perfume components contain ethyl alcohol, intake deriving from those perfume components has been taken into consideration to these values.

Moreover, the term "transparent" as used herein means those that have the L-value of 80 or greater. The L-value is a value of L in Lab color space, and is a value that can be measured as a proportion (%) of the transmitted light intensity to the irradiated light intensity of the composition with well-known colorimeters such as Color-EYE 7000 (manufactured by Gretag-Macbeth Company), or well-known spectrophotometers.

The transparent liquid composition of the present invention is one which a perfume is solubilized in a medium containing water as the main solvent by the action of a specific solubilizer. Accordingly, it is not an emulsion of a perfume.

(a) Perfume Component

The perfume used in the present invention may be a natural perfume or a synthetic perfume, and may also be a compound perfume compounded with these perfumes to achieve a desired note.

(1) Synthetic Perfume

Examples of representative synthetic perfumes include, but not limited to, alcohols, hydrocarbons, phenols, esters, carbonates, aldehydes, ketones, acetals, ethers, carboxylic acids, lactones, nitriles, and Schiff's bases.

Examples of alcohols include, but not limited to, terpene-based alcohols, aromatic alcohols, and aliphatic alcohols.

Examples of terpene-based alcohols include, but not limited to, linalool, ethyl linalool, citronellol, geraniol, nerol, terpineol, α-terpineol, dihydromyrcenol, farnesol, nerolidol, cedrol, menthol, borneol, and isobornyl cyclohexanol.

Examples of aromatic alcohols include, but not limited to, phenyl ethyl alcohol, benzyl alcohol, dimethyl benzyl carbinol, phenyl ethyl dimethyl carbinol, and phenyl hexanol.

Examples of aliphatic alcohols include, but not limited to, cis-3-hexenol, 1-(2,2,6-trimethylcyclohexyl)-3-hexanol, 1-(2-tert-butylcyclohexyloxy)-2-butanol, 2-methyl-4-(2,2,3-trimethyl-3-cyclopenten-1-yl)-2-buten-1-ol, ethyl norbornyl cyclohexanol, and 4-methyl-3-decen-5-ol.

Examples of hydrocarbons include, but not limited to, limonene, α-pinene, β-pinene, terpinene, cedrene, longifolene, and valencene.

Examples of phenols include, but not limited to, guaiacol, eugenol, isoeugenol, thymol, para cresol, vanillin, and ethyl vanillin.

Examples of esters include, but not limited to, formic acid esters, acetic acid esters, propionic acid esters, butyric acid esters, valeric acid esters, hexanoic acid esters, heptanoic acid esters, nonenoic acid esters, benzoic acid esters, cinnamic acid esters, salicylic acid esters, brassylic acid esters, tiglic acid esters, jasmonic acid esters, dihydrojasmonic acid esters, glycidic acid esters, and anthranilic acid esters.

Examples of formic acid esters include, but not limited to, linalyl formate, citronellyl formate, and geranyl formate.

Examples of acetic acid esters include, but not limited to, hexyl acetate, cis-3-hexenyl acetate, linalyl acetate, citronellyl acetate, geranyl acetate, neryl acetate, terpinyl acetate, nopyl acetate, bornyl acetate, isobornyl acetate, acetyl eugenol, acetyl isoeugenol, o-tert-butylcyclohexyl acetate, p-tert-butylcyclohexyl acetate, tricyclodecenyl acetate, benzyl acetate, phenylethyl acetate, styralyl acetate, cinnamyl acetate, dimethylbenzylcarbinyl acetate, and 3-pentyltetrahydropyran-4-yl acetate.

Examples of propionic acid esters include, but not limited to, citronellyl propionate, tricyclodecenyl propionate, allyl cyclohexyl propionate, benzyl propionate, and styrallyl propionate.

Examples of butyric acid esters include, but not limited to, citronellyl butylate, dimethylbenzylcarbinyl n-butylate, and tricyclodecenyl isobutylate.

Examples of valeric acid esters include, but not limited to, methyl valerate, ethyl valerate, butyl valerate, amyl valerate, benzyl valerate, and phenylethyl valerate. Examples of hexanoic acid esters include, but not limited to, methyl hexanoate, ethyl hexanoate, aryl hexanoate, linalyl hexanoate, and citronellyl hexanoate.

Examples of heptanoic acid esters include, but not limited to, methyl heptanoate, and aryl heptanoate.

Examples of nonenoic acid esters include, but not limited to, methyl 2-nonenoate, ethyl 2-nonenoate, and ethyl 3-nonenoate.

Examples of phenylacetic acid esters include, but not limited to, phenylethyl phenylacetate, and p-cresyl phenylacetate.

Examples of benzoic acid esters include, but not limited to, methyl benzoate, and benzyl benzoate.

Examples of cinnamic acid esters include, but not limited to, methyl cinnamate, and benzyl cinnamate.

Examples of salicylic acid esters include, but not limited to, methyl salicylate, n-hexyl salicylate, cis-3-hexenyl salicylate, cyclohexyl salicylate, and benzyl salicylate.

Examples of brassylic acid esters include, but not limited to, ethylene brassylate.

Examples of tiglic acid esters include, but not limited to, geranyl tiglate, 1-hexyl tiglate, and cis-3-hexenyl tiglate.

Examples of jasmonic acid esters include, but not limited to, methyl jasmonate.

Examples of dihydrojasmonic acid esters include, but not limited to, methyl dihydrojasmotate.

Examples of anthranilic acid esters include, but not limited to, methyl anthranilate, ethyl anthranilate, and dimethyl anthranilate (methyl N-methyl anthranilate).

Examples of other esters include, but not limited to, ethyl 2-methyl butylate, methyl atrarate, allyl cyclohexyl glycolate, allyl 2-pentyroxyglycolate, ethyl 2-cyclohexylpropionate, 2-methylpentyl 2-methyl valerate, ethyl 3,5,5-trimethylhexanoate, ethyl 2-ethylcaproate, and methyl 2,4-dihydroxy-3,6-dimethylbenzoate.

Examples of carbonates include, but not limited to, cis-3-hexenylmethylcarbonate, methylcyclooctylcarbonate, and ethyl 2-tert-butylcyclohexylcarbonate.

Examples of aldehydes include, but not limited to, n-octanal, n-nonanal, n-decanal, n-undecanal, n-dodecanal, 2-methylundecanal, 10-undecenal, citronellal, citral, hydroxycitronellal, 2,4-dimethyl-3-cyclohexenylcarboxyaldehyde, dimethyl-3-cyclohexenyl-1-carboxyaldehyde, benzaldehyde, phenylacetalaldehyde, phenylpropylaldehyde, cinnamic aldehyde, dimethyltetrahydrobenzaldehyde, Burgeonal (product name of Givaudan SA, 3-(p-tert-butylphenyl)-propanal), hydroxymyrac aldehyde, 2-cyclohexylpropanal, Lilial (product name of Givaudan SA, p-tert-butyl-α-methylhydrocinnamic aldehyde), p-isopropyl-α-methylhdrocinnamic aldehyde, Floralozone (product name of IFF Inc., p-ethyl-α-α-dimethylhydrocinnamic aldehyde), α-amyl cinnamic aldehyde, α-hexyl cinnamic aldehyde, heliotropine, and Helional (product name of IFF Inc., α-methyl-3,4-methylenedioxyhydro cinnamic aldehyde).

Examples of ketones include, but not limited to, α-ionone, β-ionone, γ-ionone, α-methyl ionone, β-methyl ionone, γ-methyl ionone, damascenone, nethylheptenone, 4-methylene-3,5,6,6-tetramethyl-2-heptanone, acetophenone, amylcyclopentanone, dihydro jasmone, rose ketone, carvone, menthone, camphor, acetyl cedrene, isolongifolanone, nootkatone, benzyl acetone, anisyl acetone, methyl β-naphthyl ketone, 2,5-dimethyl-4-hydroxy-3(2H)-furanone, maltol, muscone, civetone, cyclopentadecanone, Calone (product name of Firmenich SA, 7-methyl-3,5-dihydro-2H-benzodioxepin-3-on), raspberry ketone, and heliotropylacetone.

Examples of acetals include, but not limited to, acetaldehyde ethylphenylpropyl acetal, citral diethyl acetal, phenylacetaldehyde glyceryl acetal, phenylacetaldehyde dimethyl acetal, and ethyl acetoacetate ethyleneglycol acetal.

Examples of ethers include, but not limited to, cedryl methyl ether, estragole, anethole, β-naphthyl methyl ether, β-naphthyl ethyl ether, limonene oxide, rose oxide, nerol oxide, 1,8-cineole, rose furan, [3aR-(3aα,5aβ,9aα,9bβ)]-dodecahydro-3a,6,6,9a-tetramethylnaphtho[2.1-b]furan, 3,3,5-trimethylcyclohexylethyl ether, and Galaxolide (product name of IFF Inc., hexamethylhexahy drocy clopentabenzopyran).

Examples of carboxylic acids include, but not limited to, benzoic acid, phenylacetic acid, cinnamic acid, hydrocinnamic acid, butyric acid, and 2-hexenoic acid.

Examples of lactones include, but not limited to, γ-decatactone, δ-decalactone, γ-valerolactone, γ-nonalactone, γ-undecalactone, δ-hexalactone, γ-jasmolactone, whisky lactone, coumarin, cyclopentadecanolide, cyclohexadecanolide, ambrettolide, 11-oxahexadecanolide, and butylidenephthalide.

Examples of nitriles include, but not limited to, geranyl nitrile, citronitrile, and dodecanenitrile.

Examples of Schiff's bases include, but not limited to, Aurantiol, and Ligantral.

Alcohols, hydrocarbons, phenols, esters, aldehydes, ketones, acetals, and ethers are preferred among the above, and alcohols and esters are particularly preferred.

(2) Natural Perfume

Natural perfumes that can be used in the present invention are not particularly limited. Examples thereof include, but not limited to: natural essential oils such as anise seed, ylang-ylang, elemi, orris, orange, galvanum, clary sage, clove, coriander, sandalwood, citronella, cinnamon, jasmine, spearmint, cedar wood, geranium, celery, tangerine, tonka beans, neroli, violet, patchouli, peach, vetiver, petitgrain, peppermint, Peru balsam, bergamot, *eucalyptus*, lilac, raspberry, lavender, lily of the valley, lemon, lemongrass, lime, rose, etc.; and animal perfumes such as amber, castoreum, civet, musk, etc. Moreover, plant extracts such as peppermint oils may be used.

(3) Compound Perfume

Compound perfumes that can be used in the present invention are not particularly limited. Examples thereof include compound perfumes having notes of citrus notes, floral notes, fruity notes, herbal notes, spicy notes, green notes, woody notes, balsamic notes, aldehydic notes, minty notes, aromatic notes, earthy notes, mossy notes, honey notes, leather notes, animalic notes, amber notes, and/or musky notes.

Among the above, alcohols, hydrocarbons, and aldehydes can be used preferably in the present invention. Specific examples of the compounds include, but not limited to, phenylethyl alcohol, n-undecanal, limonene, geranium, and peppermint oil.

The perfume component (a) relative to the transparent liquid composition according to the present invention can be blended at 3-20% by mass, preferably 5-15% by mass, and more preferably 7-12% by mass. This is because: when it is less than 3% by mass, intensity of fragrance and lasting time may not be sufficient; and the concentration of perfume being 20% by mass is almost the limit amount in aqueous solvents.

(b) Hydrogenated castor oil to which 30-60 moles of polyoxyethylene is added, and (c) alkanol obtained by addition polymerization of 20-30 moles of polyoxypropylene and 20-30 moles of polyoxyethylene In the present invention, a hydrogenated castor oil to which 30-60 moles of polyoxyethylene is added, and an alkanol obtained by addition polymerization of 20-30 moles of polyoxypropylene and 20-30 moles of polyoxyethylene can be used as the main solubilizer of the perfume component. The component (b) is a surfactant generally used for solubilizing perfumes in aqueous solvents. Moreover, the component (c) is a surfactant known to be used for solubilizing perfumes together with the component (b). Here, the alkanol is a general name for a compound of which one or more of a hydrogen of the alkane is substituted with a hydroxyl group, and it may also be referred to as a saturated alcohol, or a paraffin alcohol.

The average number of moles added of polyoxyethylene in the component (b) is preferably 30-60, more preferably 35-45, and most preferably 40.

The most preferred example of the compound that can be preferably used as the component (c) is PPG-26-Buteth-26

(INCI name: PPG-26-Butheth-26, butanol obtained by addition polymerization of 26 moles of polyoxypropylene and 26 moles of polyoxyethylene).

The blending amount of the components (b) and (c) in the present composition can be adjusted in accordance with the blending amount of the perfume to be solubilized; however, it may be about 3-30% by mass, preferably 5-20% by mass, and more preferably 7-15% by mass. When the blending amount is less than 3% by mass, solubilization may not be sufficient, and the composition may not become transparent depending on the blending amount of the perfume. When it is greater than 30% by mass, stickiness may be extremely strong, or aggregates of higher order may be formed to be gelatinized.

The blending ratio ((c)/(b)) of the component (c) to the component (b) is preferably 0.7 or greater, more preferably 0.7-2.5, and further preferably 0.8-2.0. This is because, when the blending ratio is smaller than 0.7, solubilization may not be sufficient, and the composition may not become transparent depending on the blending amount of the perfume.

(d) Surfactant having IOB value of 0.70-1.20

A surfactant having an IOB value (=Inorganic-value/Organic-value) of 0.70-1.20 can be used as an auxiliary solubilizer for solubilizing the perfume in the present invention. The IOB value (Inorganic Organic Balance) is a value of which the inorganic value of the compound is divided by the organic value (=Inorganic-value/Organic-value), and is generally used as an index to show the balance between inorganicity and organicity. Here, the inorganic value (abbreviated as IV) and the organic value (abbreviated as OV) are values defined based on the organic conceptional diagram (Atsushi FUJITA, Prediction of Organic Compounds by Conceptional diagram, Journal of Japanese Chemistry Vol. 11, No. 10 (1957) 719-715)). In this organic conceptional diagram, the property of a compound in terms of physical chemistry is considered in such a way that the property that depends much on Van Der Waals force is called "Organicity" and the one that depends much on electric affinity is called "Inorganicity".

Therefore, the IOB value is a value given as an angle from the origin (i.e., tan a) in a graph having the inorganic value as the vertical axis and the organic value as the horizontal axis. The closer the IOB value is to zero, the more non-polar the organic compound is (lipophilicity and organicity are greater), and the larger the value is, the more polar the organic compound is (hydrophilicity and inorganicity are greater).

It is more preferred that the auxiliary solubilizer in the present invention has the square root of the sum of the square of the inorganic value and the square of the organic value (this value may be called as "d-value" herein) of 2000-5000. This is because it is confirmed that a large amount of perfume can be solubilized within this range.

The d-value is represented as a distance from the origin in the organic conceptional diagram, and is a value that correlates with the molecular weight if it is a compound of same series (reference: Catalogue of Nihon Emulsion Co., Ltd., "The Effective Formulation Development Using the "Organic Conceptual diagram"", p 2, https://www.nihon-emulsion.co.jp/shared/pdf/tech/emulsification_prescription.pdf).

Examples of the compounds that can be used preferably as the component (d) include, but not limited to: decyltetradecanol and phytosterol obtained by addition polymerization of ethylene oxide and propylene oxide; and polyoxyethylene hydrogenated castor oil esterified with pyroglutamic acid and isostearic acid.

In the present invention, one type or two or more types of a surfactant having the above-described IOB value of 0.70-1.20 can be used as the auxiliary solubilizer.

The blending amount of the surfactant (d) having the IOB value of 0.70-1.20 in the present invention relative to the whole composition is preferably 0.01-10% by mass, more preferably 0.3-5% by mass, and further more preferably 0.5-3% by mass. When it is less than 0.01% by mass or exceeds 10% by mass, the perfume may not be solubilized sufficiently, and the composition may not become transparent.

(e) Aqueous Components Other than Ethyl Alcohol

The component (e) is a solvent of the composition according to the present invention. It is sufficient if the component (e) is an aqueous component other than ethyl alcohol, and it is preferably water. This water may be ion-exchanged water, purified water, tap water, or the like.

Since the component (e) is a solvent, the blending amount thereof becomes the balance of other components; however, it is preferably 40% by mass or greater relative to the whole composition.

Components generally used in liquid cosmetics can be blended in the present invention whithin a range of not inhibiting the effect of the present invention. Examples of such components include, but not limited to, moisturizers, vitamins, antioxidants, drugs, stabilizers, polymer compounds, and colorants.

Moisturizers are not particularly limited. Examples thereof include, but not limited to: saccharides or polyols such as sucrose, sorbitol, glycerin, 1,3-butylene glycol, propylene glycol, and dipropylene glycol; polyether based compounds obtained by addition-polymerizing 2-100 moles of propylene oxide and 50 moles or less of ethylene oxide to a polyhydric alcohol core having three or more hydroxyl groups in the molecule; ethyl gluteth-10; chondroitin sulfate; hyaluronic acid; mucoitin sulfuric acid; atelocollagen; cholesteryl 12-hydroxystearate; bile acid monosalt; dl-pyrrolidone carboxylic acid monosalt; short-chained soluble collagen; *Rosa roxburghii* extract; *Achillea millefolium* extract; glycols such as propylene glycol, dipropylene glycol, 1,3-butylene glycol, 1,4-butylene glycol, diethylene glycol, triethylene glycol, and polyethylene glycols having greater molecular weights than these; glycerin; diglycerin; polyglycerins having greater molecular weights than these; sugar alcohols such as sorbitol, mannitol, maltitol, xylitol, and erythritol; sugars such as fructose, glucose, galactose, maltose, lactose, and trehalose; and polypropylene glycol-polyethelene glycol copolymers or dimethyl ethers thereof.

In particular, glycerin, 1,3-butylene glycol, propylene glycol, dipropylene glycol, polyethylene glycol having the molecular weight of 1000 or greater, polypropylene glycol-polyethylene glycol copolymers and dimethyl ethers thereof can be used preferably among the above.

It is preferred that the transparent liquid composition of the present invention does not substantially contain a surfactant other than the components (b), (c) and (d). The term "substantially" as used herein means 1% by mass or less, and preferably 0.5% by mass or less.

Moreover, it is preferred that the transparent liquid composition of the present invention does not substantially contain an oil component other than the component (a). The term "substantially" as used herein means 5% by mass or less, preferably 3% by mass or less, and more preferably 1% by mass or less.

The transparent liquid composition of the present invention can be preferably used as fragrances, and particularly preferred as aromatic cosmetics such as perfumes (parfums), Eau de parfums, Eau de toilettes, Eau de colognes, etc. It can also be used as household air fresheners.

The transparent liquid composition of the present invention does not require special devices, and can be basically produced by mixing the components.

EXAMPLES

Examples according to the present invention are described in the following; however, the present invention is not limited thereto. The blending amounts in the following formulations are in "% by mass" unless otherwise specified.

First, an evaluation method of the compositions performed in the examples is described.

<Evaluation Method>

In the Examples, it was determined as "the perfume is completely solubilized" when it was determined as "transparent" in the following (1) and "transparent and uniform" in (2), (1) Appearance of the Composition The composition immediately after production was observed visually to determine whether it was "clouded" or not. The composition determined not to be clouded was filled to a quartz glass cell (optical path length: 10 mm) without dilution, and the L-value was measured with an integrating-sphere photometer (Color-EYE 7000 (manufactured by Gretag-Macbeth Company)). The final determination criteria are as follows.

Clouded: Clouding was observed visually, or the L-value being less than 80

Transparent: the L-value being 80 or greater (2) State after Centrifugal Treatment The composition immediately after production was subjected to a centrifugal treatment (2000 rpm, 30 minutes), and the state after the centrifugal treatment was observed visually. Those that sedimentation occurred were determined as "separated", and those that sedimentation was not confirmed (i.e., those that were transparent and uniform) were determined as "transparent and uniform".

The compounds indicated with asterisks in the tables are as follows.

*1: Mixed perfume 1

A mixed perfume consisting of 50% of limonene and 50% of undecanal.

*2: Mixed perfume 2

A mixed perfume consisting of 30% of limonene, 35% of phenylethyl alcohol, and 35% of undecanal.

Test Example 1: Investigation of the Types of Auxiliary Solubilizers

Fragrances (may be simply called as compositions in the following) having the formulations of Table 1 were produced to evaluate for the evaluation items. The results are shown in Table 1.

TABLE 1

| | | | Test example | | | | |
|---|---|---|---|---|---|---|---|
| | | Component | Compar. example 1 | Example 1 | Example 2 | Example 3 | Example 4 |
| Formulation | Perfume | Mixed perfume 1*1 | 5.0 | 5.0 | 5.0 | 5.0 | 5.0 |
| | Main solubilizer | PEG-40 Hydrogenated Castor Oil | 4.50 | 3.15 | 3.15 | 3.15 | 3.15 |
| | | PPG-26-Buteth-26 | 4.50 | 3.15 | 3.15 | 3.15 | 3.15 |
| | Auxiliary solubilizer | PPG-13 Decyltetradeceth-24 | — | 2.7 | — | — | — |
| | | PPG-20 Decyltetradeceth-10 | — | — | 2.7 | — | — |
| | | PPG-7/PEG-30 Phytosterol | — | — | — | 2.7 | — |
| | | Hydrogentated Castor Oil PCA Isostearate | — | — | — | — | 2.7 |
| | | PEG-60 Glyceryl Isostearate | — | — | — | — | — |
| | | PEG-8 Distearate | — | — | — | — | — |
| | | Polyglyceryl-2 Distearate | — | — | — | — | — |
| | | Sorbitan Sesquiisostearate | — | — | — | — | — |
| | | PEG-100 Stearate | — | — | — | — | — |
| | Solvent | Ion-exhanged water | Balance | Balance | Balance | Balance | Balance |
| | Total | | 100.0 | 100.0 | 100.0 | 100.0 | 100.0 |
| Evaluation | (1) Appearance (25° C.) | | Clouded | Transparent | Transparent | Transparent | Transparent |
| | (2) State after centrifugal treatment | | Separated | Transparent & uniform | Transparent & uniform | Transparent & uniform | Transparent & uniform |

TABLE 1-continued

|  | Component | | Compar. example 2 | Compar. example 3 | Compar. example 4 | Compar. example 5 | Compar. example 6 |
|---|---|---|---|---|---|---|---|
| Formulation | Perfume | Mixed perfume 1*[1] | 5.0 | 5.0 | 5.0 | 5.0 | 5.0 |
|  | Main solubilizer | PEG-40 Hydrogenated Castor Oil | 3.15 | 3.15 | 3.15 | 3.15 | 3.15 |
|  |  | PPG-26-Buteth-26 | 3.15 | 3.15 | 3.15 | 3.15 | 3.15 |
|  | Auxiliary solubilizer | PPG-13 Decyltetradeceth-24 | — | — | — | — | — |
|  |  | PPG-20 Decyltetradeceth-10 | — | — | — | — | — |
|  |  | PPG-7/PEG-30 Phytosterol | — | — | — | — | — |
|  |  | Hydrogentated Castor Oil PCA Isostearate | — | — | — | — | — |
|  |  | PEG-60 Glyceryl Isostearate | 2.7 | — | — | — | — |
|  |  | PEG-8 Distearate | — | 2.7 | — | — | — |
|  |  | Polyglyceryl-2 Distearate | — | — | 2.7 | — | — |
|  |  | Sorbitan Sesquiisostearate | — | — | — | 2.7 | — |
|  |  | PEG-100 Stearate | — | — | — | — | 2.7 |
|  | Solvent | Ion-exhanged water | Balance | Balance | Balance | Balance | Balance |
| Evaluation | Total | | 100.0 | 100.0 | 100.0 | 100.0 | 100.0 |
|  | (1) Appearance (25° C.) | | Clouded | Clouded | Clouded | Clouded | Clouded |
|  | (2) State after centrifugal treatment | | Separated | Separated | Separated | Separated | Separated |

Table 1 shows that, in the composition that blended only the main solubilizer (PPG-26-Buteth-26 and PEG-40 Hydrogenated Castor Oil) as the solubilizer, 5.0% by mass of the perfume was emulsified without being solubilized, and it resulted in a clouded appearance (Comparative example 1, Evaluation (1)). The fact of the perfume not being solubilized in the composition of Comparative example 1 was also confirmed from the fact that sedimentation occurred after the centrifugal treatment (Comparative example 1, Evaluation (2)).

Whereas, in the composition blended with PPG-13 Decyltetradeceth-24 (Example 1), PPG-20 Decyltetradeceth-10 (Example 2), PPG-7/PEG-30 Phytosterol (Example 3), or Hydrogenated Castor Oil PCA Isostearate (Example 4) as the auxiliary solubilizer, they resulted in transparent appearances, and no sedimentation occurred after the centrifugal treatment. Therefore, it was confirmed that 5.0% by mass of the perfume were solubilized in water in these compositions.

On the other hand, in the compositions blended with PEG-60 Glyceryl Isostearate (Comparative example 2), PEG-8 Distearate (Comparative example 3), Polyglyceryl-2 Distearate (Comparative example 4), Sorbitan Sesquiisostearate (Comparative example 5), and PEG-100 Stearate (Comparative example 6), they resulted in clouded appearances, and sedimentation occurred after the centrifugal treatment. Therefore, it was confirmed that 5.0% by mass of the perfume did not solubilize in water in these compositions.

From the above results, it was shown that the perfume could be solubilized in water by adding a specific surfactant as the auxiliary solubilizer even if the perfume could not be solubilized in water only with the main solubilizer.

As shown in Table 2 below, it was confirmed that the surfactant used as the auxiliary solubilizer in Table 1 could not solubilize the perfume in water when the main solubilizer was not present, i.e., when it was used alone.

TABLE 2

|  | Component | | Compar. example 7 | Compar. example 8 | Compar. example 9 | Compar. example 10 | Compar. example 11 | Compar. example 12 | Compar. example 13 | Compar. example 14 |
|---|---|---|---|---|---|---|---|---|---|---|
| Formulation | Perfume | Mixed perfume 1*[1] | 5.0 | 5.0 | 5.0 | 5.0 | 5.0 | 5.0 | 5.0 | 5.0 |
|  | Main solubilizer | PEG-40 Hydrogenated Castor Oil | — | — | — | — | — | — | — | — |
|  |  | PPG-26-Buteth-26 | — | — | — | — | — | — | — | — |
|  | Auxiliary solubilizer | PPG-20 Decyltetradeceth-10 | 9.0 | — | — | — | — | — | — | — |
|  |  | PPG-7/PEG-30 Phytosterol | — | 9.0 | — | — | — | — | — | — |

TABLE 2-continued

| | Component | | Compar. example 7 | Compar. example 8 | Compar. example 9 | Compar. example 10 | Compar. example 11 | Compar. example 12 | Compar. example 13 | Compar. example 14 |
|---|---|---|---|---|---|---|---|---|---|---|
| | | Hydrogentated Castor Oil PCA Isostearate | — | — | 9.0 | — | — | — | — | — |
| | | PEG-60 Glyceryl Isostearate | — | — | — | 9.0 | — | — | — | — |
| | | PEG-8 Distearate | — | — | — | — | 9.0 | — | — | — |
| | | Polyglyceryl-2 Distearate | — | — | — | — | — | 9.0 | — | — |
| | | Sorbitan Sesquiisostearate | — | — | — | — | — | — | 9.0 | — |
| | | PEG-100 Stearate | — | — | — | — | — | — | — | 9.0 |
| | Solvent | Ion-exhanged water | Balance | Balance | Balance | Balance | Balance | Balance | Balance | Balance |
| | Total | | 100.0 | 100.0 | 100.0 | 100.0 | 100.0 | 100.0 | 100.0 | 100.0 |
| Evaluation | (1) Appearance (25° C.) | | Clouded | Clouded | Clouded | Clouded | Clouded | Clouded | Clouded | Clouded |
| | (2) State after centrifugal treatment | | Separated | Separated | Separated | Separated | Separated | Separated | Separated | Separated |

Test Example 2: Investigation of Physical Properties of Auxiliary Solubilizers

Differences in physical properties between the auxiliary solubilizer that can solubilize the perfume in water by using it together with the main solubilizer and the auxiliary solubilizer that does not achieve such effect were investigated.

Table 3 shows the organic values, the inorganic values, the IOB values, and the d-values of each solubilizer (the organic values, inorganic values and d-values are rounded off to the nearest tenth). Moreover, with respect to the auxiliary solubilizers, Table 3 also shows the appearances of the compositions prepared in accordance with the formulations of Test example 1.

TABLE 3

| | Solubilizer | Physical property | | | | Appearance of perfume composition |
|---|---|---|---|---|---|---|
| | | Organic value | Inorganic value | tan α | d | |
| Main solubilizer | 1. PPG-26-Buteth-26 | 2680 | 2520 | 0.94 | 3680 | |
| | 2. PEG-40 Hydrogenated Castor Oil | 2740 | 3320 | 1.21 | 4300 | |
| Auxiliary solubilizer | 3. Polyglyceryl-2 Distearate (Comparative example 4) | 820 | 340 | 0.41 | 890 | Clouded |
| | 4. Sorbitan Sesquiisostearate (Comparative example 5) | 650 | 370 | 0.57 | 750 | |
| | 5. PEG-8 Distearate (Comparative example 3) | 1020 | 650 | 0.63 | 1200 | |
| | 6. PPG-20 Decyltetradeceth-10 (Example 2) | 1630 | 1250 | 0.76 | 2060 | Transparent |
| | 7. PPG-13 Decyltetradeceth-24 (Example 1) | 2210 | 2160 | 0.98 | 3090 | |
| | 8. Hydrogenated Castor Oil PCA Isostearate (Example 4) | 3190 | 3450 | 1.08 | 4700 | |
| | 9. PPG-7/PEG-30 Phytosterol (Example 3) | 2160 | 2520 | 1.17 | 3320 | |
| | 10. PEG-100 Stearate (Comparative example 6) | 4360 | 7590 | 1.74 | 8750 | Clouded |
| | 11. PEG-60 Glyceryl Isostearate (Comparative example 2) | 2810 | 4600 | 1.64 | 5390 | |

In Table 3, the auxiliary solubilizers are listed in ascending order of the IOB values. Accordingly, it shows a relationship that the appearances of the compositions became transparent when the surfactants (No. 6-9) having the IOB values of 0.76-1.17 were used as the auxiliary solubilizer, and the appearances of the compositions became clouded when the surfactants (No. 3-5, 10-11) having the IOB values that are out the above-identified range were used as the auxiliary solubilizer.

Figure 1:
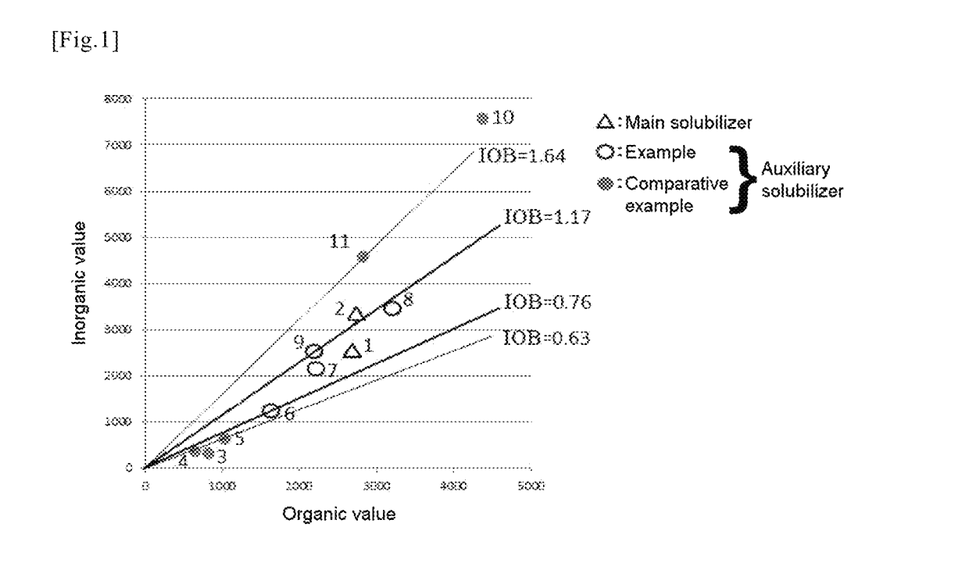
FIG. 1 is a graph plotted with IOB values of the solubilizers, and shows straight lines (four lines) that connect the plots of PEG-8 Distearate (IOB=0.63, No. 5), PPG-20 Decyltetradeceth-20 (IOB=0.76, No. 6), PPG-7/PEG-30 Phytosterol (10B=1.17, No. 9), and Oleth-20 (IOB=1.33, No. 10) and the origin, respectively.

FIG. 1 shows a graph plotted with the IOB values of the solubilizers. In FIG. 1, lines that respectively connected the plots of PEG-8 Distearate (No. 5), PPG-20 Decyltetradeceth-20 (No. 6), PPG-7/PEG-30 Phytosterol (No. 9) and PEG-60 Glyceryl Isostearate (No. 11) to the origin are shown.

Accordingly, the auxiliary solubilizer that can be used in the present invention is the surfactant having the IOB value within the range of 0.70-1.20, preferably 0.75-1.17, and it is more preferred when the d-value is within the range of 2000-5000.

Test Example 3: Investigation of the Blending Ratio of the Main Solubilizer and the Auxiliary Solubilizer Next, the blending ratio of the main solubilizer and the auxiliary solubilizer was investigated. Compositions having the formulations of Table 4 were produced to evaluate for the evaluation items. The results are shown in Table 4.

TABLE 4

| | | | Test example | | | | | | | |
|---|---|---|---|---|---|---|---|---|---|---|
| | Component | | Compar. example 1 | Compar. example 15 | Example 5 | Example 6 | Example 7 | Example 8 | Example 1 | Compar. example 16 |
| Formulation | Perfume | Mixed perfume*[1] | 5.0 | 5.0 | 5.0 | 5.0 | 5.0 | 5.0 | 5.0 | 5.0 |
| | Main solubilizer | PEG-40 Hydrogenated Castor Oil | 4.50 | 4.455 | 4.275 | 4.05 | 3.825 | 3.60 | 3.15 | 2.70 |
| | | PPG-26-Buteth-26 | 4.50 | 4.455 | 4.275 | 4.05 | 3.825 | 3.60 | 3.15 | 2.70 |
| | Auxiliary solubilizer | PPG-13 Decyltetradeceth-24 | — | 0.09 | 0.45 | 0.90 | 1.35 | 1.80 | 2.70 | 3.60 |
| | Medium | Ion-exhanged water | Balance | Balance | Balance | Balance | Balance | Balance | Balance | Balance |
| | Total | | 100 | 100 | 100 | 100 | 100 | 100 | 100 | 100 |
| Evaluation | (1) Appearance (25° C.) | | Clouded Separated | Clouded Separated | Transparent | Transparent | Transparent | Transparent | Transparent | Clouded Separated |
| | (2) State after centrifugal treatment | | | | Transparent & uniform | Transparent & uniform | Transparent & uniform | Transparent & uniform | Transparent & uniform | |
| | (3) Main solubilizer | | 9.00 | 8.91 | 8.55 | 8.10 | 7.65 | 7.20 | 6.30 | 5.40 |
| | (4) Auxiliary solubilizer/ main solubilizer | | | 0.01 | 0.05 | 0.11 | 0.18 | 0.25 | 0.43 | 0.67 |

In FIG. 1, the auxiliary solubilizers (No. 6-9) that can make the composition transparent are all present between (and on) the two straight lines of the IOB value=0.76 and the IOB value=1.17. Whereas, the auxiliary solubilizers (No. 3-5, 10-11) that make the composition clouded are all present below (and on) the straight line of the IOB value=0.63, or above (and on) the straight line of the IOB value=1.64.

Therefore, it became apparent that the solubilizer that cooperates with the main solubilizer (PEG-40 hydrogenated castor coil and PPG-26-Buteth-26) to make the perfume to solubilize in water is the surfactant having the IOB value within the range of 0.70-1.20, and preferably 0.75-1.17.

Figure 2:
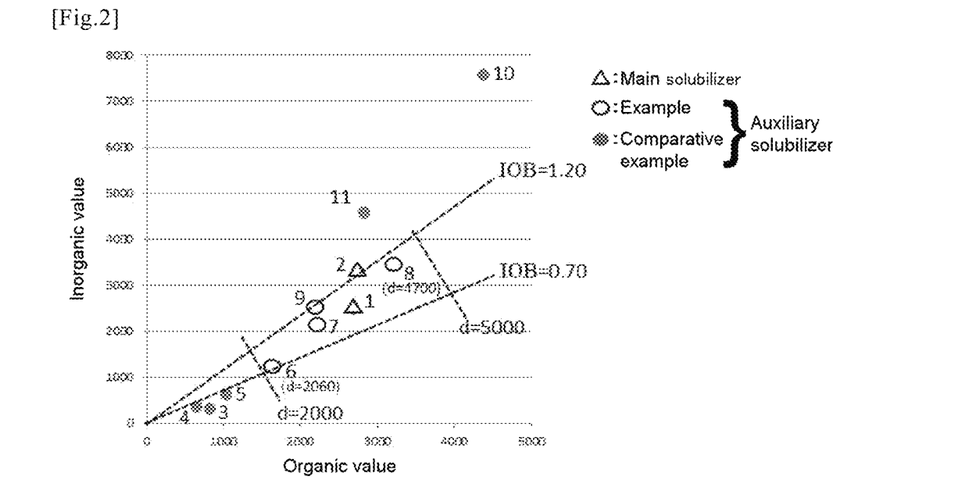
FIG. 2 is a graph plotted with IOB values of the solubilizers, and shows straight lines (four dotted lines) that represent the upper limit value and the lower limit value of IOB values of the auxiliary solubilizer of the present invention, and the upper limit value and the lower limit value of the value preferred as the d-value of the auxiliary solubilizer of the present invention.

FIG. 2 shows two straight lines (dotted lines) of the IOB value=0.70 and the IOB value=1.20. The auxiliary solubilizers that can be used preferably in the present invention are the solubilizers (having the IOB values) plotted between the two straight lines.

Furthermore, when the d-value is considered, FIG. 2 shows that the d-values of the auxiliary solubilizers (No. 6-9) that can make the composition transparent are within the range of 2060-4700.

Table 4 shows that the composition having the blending ratio of the auxiliary solubilizer to the main solubilizer (=(4) auxiliary solubilizer/main solubilizer) of 0.01 became clouded, and sedimentation occurred by the centrifugal treatment (Comparative example 15). Whereas, the compositions having the blending ratio within the range of 0.05-0.43 were transparent, and remained transparent and uniform after the centrifugal treatment (Examples 5-8, 1). On the other hand, the composition having the blending ratio of 0.67 became clouded, and sedimentation occurred after the centrifugal treatment (Comparative example 16).

Accordingly, it became apparent that, in order to obtain an aqueous transparent liquid composition by solubilizing a perfume, the blending ratio of the auxiliary solubilizer to the main solubilizer needs to be 0.03-0.60, preferably 0.04-0.50, and more preferably 0.05-0.45.

Test Example 4: Investigation of the Blending Ratio of Two Components of the Main Solubilizer The blending ratio of PEG-40 Hydrogenated Castor Oil and PPG-26-Buteth-26 that constitute the main solubilizer was investigated. The compositions having the formulations of Table 5 were produced to evaluate for the evaluation items. The results are shown in Table 5.

TABLE 5

| | Component | | Example 9 | Example 10 | Example 11 | Compar. example 17 |
|---|---|---|---|---|---|---|
| Formulation | Perfume | Mixed perfume 1*[1] | 5.0 | 5.0 | 5.0 | 5.0 |
| | Main solubilizer | PPG-26-Buteth-26 | 4.86 | 4.26 | 3.66 | 3.06 |
| | | PEG-40 Hydrogenated Castor Oil | 3.24 | 3.84 | 4.44 | 5.04 |
| | Auxiliary solubilizer | PPG-13 Decyltetradeceth-24 | 0.90 | 0.90 | 0.90 | 0.90 |
| | Medium | Ion-exchanged water | Balance | Balance | Balance | Balance |
| | Total | | 100 | 100 | 100 | 100 |
| Evaluation | (1) Appearance (25° C.) | | Transparent | Transparent | Transparent | Clouded |
| | (2) State after centrifugal treatment | | Transparent & uniform | Transparent & uniform | Transparent & uniform | Separated |
| | (3) Main solubilizer | | 8.10 | 8.10 | 8.10 | 8.10 |
| | (4) Auxiliary solubilizer/main solubilizer | | 0.11 | 0.11 | 0.11 | 0.11 |
| | (5) PPG-26-Buteth-26/PEG-40 Hydrogenated Castor Oil | | 1.50 | 1.11 | 0.82 | 0.61 |

Table 5 shows that the compositions having the blending ratio of PPG-26-Buteth-26 to PEG-40 Hydrogenated Castor Oil (=(5) PPG-26-Buteth-26/PEG-40 Hydrogenated Castor Oil) within the range of 0.82-1.50 had transparent appearances, and remained transparent and uniform after the centrifugal treatment (Examples 9-11); however, the composition having the blending ratio of 0.61 became clouded, and sedimentation occurred by the centrifugal treatment (Comparative example 17).

Accordingly, it became apparent that, in the main solubilizer according to the present invention, the value of PPG-26-Buteth-26/PEG-40 Hydrogenated Castor Oil needs to be 0.7-2.5, preferably 0.75-2.0, and more preferably 0.8-1.7.

Test Example 5: Investigation of the Type and the Blending Amount of the Perfume Investigation was carried out by varying the types of the perfumes. The compositions having the formulations of Table 6 were produced to evaluate for the evaluation items. The results are shown in Table 6.

TABLE 6

| | Component | | Example 12 | Example 13 | Example 14 | Example 15 | Example 16 | Example 17 | Compar. example 18 | Compar. example 19 |
|---|---|---|---|---|---|---|---|---|---|---|
| Formulation | Perfume | Mixed perfume 1*[1] | 5.0 | — | — | — | — | — | — | — |
| | | Mixed perfume 2*[2] | — | 5.0 | — | — | — | — | — | — |
| | | Limonene | — | — | 5.0 | — | — | — | — | — |
| | | Undecanal | — | — | — | 5.0 | — | — | — | — |
| | | Peppermint Oil | — | — | — | — | 5.0 | — | — | — |
| | | Geranium | — | — | — | — | — | 5.0 | — | — |
| | Oil component | Mineral Oil | — | — | — | — | — | — | 5.0 | — |
| | | Dimethylpolysiloxane (6cs) | — | — | — | — | — | — | — | 5.0 |
| | Main solubilizer | PEG-40 Hydrogenated Castor Oil | 3.84 | 3.84 | 3.84 | 3.84 | 3.84 | 3.84 | 3.84 | 3.84 |
| | | PPG-26-Buteth-26 | 4.26 | 4.26 | 4.26 | 4.26 | 4.26 | 4.26 | 4.26 | 4.26 |
| | Auxiliary solubilizer | PPG-13 Decyltetradeceth-24 | 0.90 | 0.90 | 0.90 | 0.90 | 0.90 | 0.90 | 0.90 | 0.90 |
| | Medium | Ion-exhanged water | Balance | Balance | Balance | Balance | Balance | Balance | Balance | Balance |
| | Total | | 100 | 100 | 100 | 100 | 100 | 100 | 100 | 100 |
| Evaluation | (1) Appearance (25° C.) | | Transparent | Transparent | Transparent | Transparent | Transparent | Transparent | Clouded | Clouded |
| | (2) State after centrifugal treatment | | Transparent & uniform | Transparent & uniform | Transparent & uniform | Transparent & uniform | Transparent & uniform | Transparent & uniform | Separated | Separated |
| | (3) Main solubilizer | | 8.10 | 8.10 | 8.10 | 8.10 | 8.10 | 8.10 | 8.10 | 8.10 |
| | (4) Auxiliary solubilizer/main solubilizer | | 0.11 | 0.11 | 0.11 | 0.11 | 0.11 | 0.11 | 0.11 | 0.11 |
| | (6) Perfume/solubilizer (total amount) | | 0.56 | 0.56 | 0.56 | 0.56 | 0.56 | 0.56 | 0.56 | 0.56 |

When any of the mixed perfumes of which a plurality of synthetic perfumes is mixed (Examples 12, 13), the synthetic perfumes (Example 14, 15), the plant extract (Example 16), or the essential oil (Example 17) is used, the liquid compositions that have transparent appearances and remain uniform and transparent after the centrifugal treatment were obtained. Whereas, when the same amount of non-polar oils (mineral oil and silicone oil, Comparative examples 18 and 19) instead of the perfume were blended, the liquid compositions became clouded, and sedimentation occurred after the centrifugal treatment.

Accordingly, it was shown that, by using the solubilizer (the combination of the main solubilizer and the auxiliary solubilizer) according to the present invention, various perfume components, such as natural perfumes including essential oils, synthetic perfumes, and compound perfumes, can be solubilized in water to obtain a transparent liquid composition.

Figure 3:
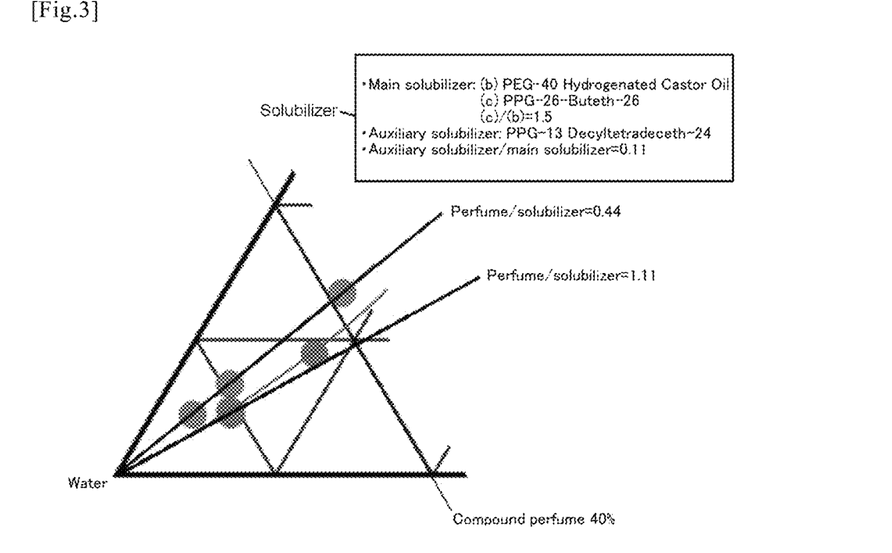
FIG. 3 is a part of a three-phase diagram of "water"-"solubilizer"-"compound perfume".

FIG. 3 shows a part of a three-phase diagram of "water"-"solubilizer"-"compound perfume". The plots in the diagram represent the transparent liquid compositions.

FIG. 3 shows that, in all compositions that became transparent liquid, the blending ratio (perfume/total solubilizers) of the perfume to the total amount of the solubilizers (=the sum of the main solubilizer and the auxiliary solubilizer) is within the range of 0.44-1.11.

Accordingly, it became apparent that, in order to obtain a transparent liquid composition that does not substantially contain ethyl alcohol, contains water as the main solvent, and has a high concentration of perfume, the blending ratio (perfume/total solubilizers) of the perfume to the total amount of the solubilizers (=the sum of the main solubilizer and the auxiliary solubilizer) is preferably within the range of 0.44-1.11.

The formulations of the examples of the transparent liquid composition according to the present invention are listed below; however, the present invention is not limited thereto. All compositions listed below had transparent appearances at 25° C., and no sedimentation occurred after the centrifugal treatment.

| Example 18: Fragrance | Blending amount (% by mass) |
|---|---|
| Mixed perfume*[1] | 15 |
| PEG-40 Hydrogenated Castor Oil | 7.9 |
| PPG-26-Buteth-26 | 7.9 |
| PPG-13 Decyltetradeceth-24 | 1.6 |
| Butylene glycol | 5 |
| Phenoxy ethanol | Suitable amount |
| Citric acid | Suitable amount |
| Sodium citrate | Suitable amount |
| EDTA-2Na | Suitable amount |
| Purified water | Balance |
| Total | 100.0 |

| Example 19: Fragrance | Blending amount (% by mass) |
|---|---|
| Mixed perfume*[1] | 18 |
| PEG-40 Hydrogenated Castor Oil | 9.5 |
| PPG-26-Buteth-26 | 7.9 |
| PPG-13 Decyltetradeceth-24 | 1.9 |
| Butylene glycol | 5 |
| Phenoxy ethanol | Suitable amount |
| Citric acid | Suitable amount |
| Sodium citrate | Suitable amount |
| EDTA-2Na | Suitable amount |
| Purified water | Balance |
| Total | 100.0 |

The invention claimed is:

1. A transparent liquid composition comprising:
    (a) 3-20% by mass of a perfume component;
    (b) a hydrogenated castor oil to which 30-60 moles of polyoxyethylene is added;
    (c) an alkanol obtained by addition polymerization of 20-30 moles of polyoxypropylene and 20-30 moles of polyoxyethylene;
    (d) one type or more of a surfactant selected from a group consisting of (i) decyltetradecanol obtained by addition polymerization of ethylene oxide and propylene oxide; (ii) phytosterol obtained by addition polymerization of ethylene oxide and propylene oxide; and (iii) polyoxyethylene hydrogenated castor oil esterified with pyroglutamic acid and isostearic acid; and
    (e) 40% by mass or greater of an aqueous component other than ethyl alcohol, wherein the blending ratio (d/(b+c)) of the component (d) to the sum of the blending amounts of the components (b) and (c) is 0.03-0.60, and
ethyl alcohol is not substantially contained in the composition.

2. The transparent liquid composition of claim 1, wherein the blending ratio (a/(b+c+d)) of the component (a) to the sum of the blending amounts of the components (b)–(d) is 0.4-1.1.

3. The transparent liquid composition of claim 1, wherein the component (b) is PEG-40 Hydrogenated Castor Oil.

4. The transparent liquid composition of claim 1, wherein the component (c) is PPG-26-Buteth-26.

5. The transparent liquid composition of claim 1, wherein the blending ratio (c/b) of the component (c) to the blending amount of the component (b) is 0.7-2.5.

6. The transparent liquid composition of claim 1, wherein an oil component other than the perfume component (a) is not substantially contained.

7. The transparent liquid composition of claim 1, wherein the component (b) is hydrogenated castor oil to which 35-45 mol polyoxyethylene is added.

8. The transparent liquid composition of claim 1, wherein the component (d) is one or more ingredient selected from the group consisting of PPG-13 decyltetradeceth-24, PPG-20 decyltetradeceth-10, PPG-7/PEG-30 phytosterol and PCA isostearic acid hydrogenated castor oil.

9. The transparent liquid composition of claim 1, wherein the composition has an L-value of 80 or more in the Lab colour system.

10. The transparent liquid composition of claim 1, wherein a content of the ethyl alcohol in the composition is less than 5% by mass.

* * * * *

UNITED STATES PATENT AND TRADEMARK OFFICE
CERTIFICATE OF CORRECTION

| | | |
|---|---|---|
| PATENT NO. | : 12,036,308 B2 | Page 1 of 1 |
| APPLICATION NO. | : 17/291161 | |
| DATED | : July 16, 2024 | |
| INVENTOR(S) | : Fukuhara et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 616 days.

Signed and Sealed this
Third Day of December, 2024

Katherine Kelly Vidal
*Director of the United States Patent and Trademark Office*